United States Patent [19]

Lehmbeck et al.

[11] Patent Number: 4,610,530
[45] Date of Patent: Sep. 9, 1986

[54] CAPACITIVE PAPER PROPERTY SENSOR FOR COPYING APPARATUS

[75] Inventors: Donald R. Lehmbeck, Penfield; Martin E. Banton, Fairport, both of N.Y.

[73] Assignee: Xerox Corporation, Stamford, Conn.

[21] Appl. No.: 685,004

[22] Filed: Dec. 21, 1984

[51] Int. Cl.$^4$ .............................................. G03G 15/00
[52] U.S. Cl. ............................... 355/14 TR; 355/3 TR
[58] Field of Search ........... 355/3 TR, 14 TR, 14 SH; 361/23 S; 324/61 P, 61 R; 73/74

[56] References Cited

U.S. PATENT DOCUMENTS

| | | | |
|---|---|---|---|
| 3,246,216 | 4/1966 | Mead et al. | 317/246 |
| 3,358,378 | 12/1967 | Downs | 34/1 |
| 3,519,922 | 7/1970 | Nash et al. | 324/61 |
| 3,704,412 | 11/1972 | Lundstrom | 324/61 R |
| 3,764,899 | 10/1973 | Peterson et al. | 324/61 R |
| 3,816,756 | 6/1974 | Bresnick | 355/14 D |
| 3,959,723 | 5/1976 | Wagner | 324/61 P |
| 4,134,147 | 1/1979 | Watanabe | 361/235 |
| 4,282,480 | 8/1981 | Fujito et al. | 324/61 R |
| 4,301,401 | 11/1981 | Roof et al. | 324/61 R |

Primary Examiner—Arthur T. Grimley
Assistant Examiner—David Warren
Attorney, Agent, or Firm—Frederick E. McMullen

[57] ABSTRACT

A capacitive paper property sensor for sensing the moisture content of copy sheets in a xerographic system in which a copy sheet feed roll pair are made overlong to provide a non-feeding nip segment in addition to the feeding nip segment; a capacitor in each non-feeding and feeding nip segment with the capacitor plates thereof in substantially the same plane as the roll surface, each capacitor providing capacitance signals reflecting the current size of the roll nip in both the non-feeding and feeding nip segments; comparator means for comparing the capacitance signal output of one capacitor with the capacitance signal output of the other capacitor to provide a signal representative of the moisture content of the copy sheet passing through the roll nip; a memory for storing various moisture content-/control signal relationships to thereby enable the moisture signal to be converted to a control signal; and control means for adjusting at least one of the xerographic system operating components in response to the control signal.

In a second embodiment, the capacitor in the feeding nip segment comprises a succession of capacitors across the length of the feeding nip segment to provide a profile of the copy sheet moisture content across the sheet width.

8 Claims, 6 Drawing Figures

DIELECTRIC CONSTANT Vs. MOISTURE CONTENT

CAPACITIVE PAPER PROPERTY SENSOR FOR COPYING APPARATUS

The invention relates to sensing the moisture content of copy sheets during the copying process, and more particularly to a capacitive type moisture sensor for this purpose.

In xerographic based electrostatic type copying and printing machines, the physical properties of the copy sheets on which the copies are made, which is typically paper, are often determinative of machine copy quality and operating reliability. One property in this category that ofttimes directly and immediately affects machine operation and copy quality is the moisture content of the copy sheet. This can be understood by considering that when the moisture content of the copy sheets is very low, the copy sheets tend to accumulate excessive static charges which, unless accounted for, can interfere with the ability to electrostatically transfer the developed images from the machine photoreceptor to the copy sheet. The result is poor and uneven copy quality and excessive service calls. On the other hand, if the moisture content of the copy sheets is high, incomplete fusing or fixing of the copies can result; this due to the fact that high moisture content requires more heat and higher fusing temperatures to drive off the excess moisture than is the case where the moisture content is low.

The invention seeks to remedy the foregoing problems by providing an electrostatic copying or printing apparatus having a copy sheet path, there being at least one copy sheet feed roll pair for transporting copy sheets along the copy sheet path, the rolls of the copy sheet feed roll pair being axially extended to form a first nip segment between which the copy sheets being fed pass, and a second nip segment outside of the copy sheet path; a first capacitor for generating a capacitance signal representative of the nip size in the first nip segment; a second capacitor for generating a capacitance signal representative of the nip size in the second nip segment; means for comparing the signal outputs of the first and second capacitors to determine the dielectric constant of the copy sheet passing through the first nip segment; and means for converting the dielectric constant to a control signal representing the copy sheet moisture content.

IN THE DRAWINGS

Figure 1:
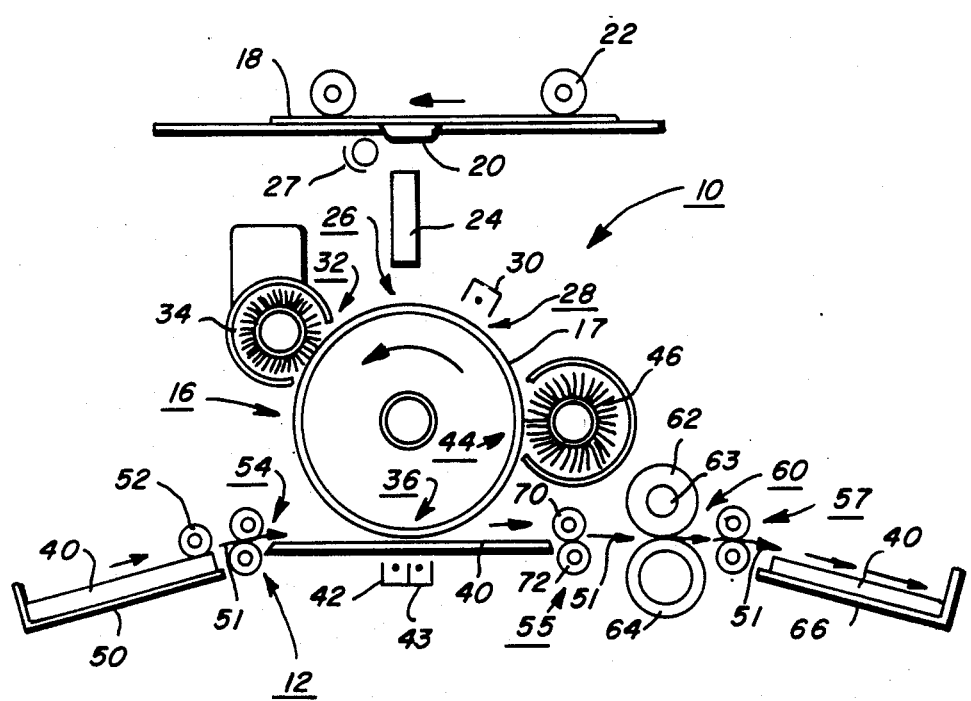
FIG. 1 is a schematic view of a copying machine of the type adapted to incorporate the copy sheet moisture sensor of the present invention.

Referring particularly to FIG. 1 of the drawings, there is shown an exemplary xerographic copying or reproduction machine, designated generally by the numeral 10, incorporating the copy sheet moisture sensor, designated generally by the numeral 12, of the present invention. Copying machine 10 includes a suitable photoreceptor, shown here in the form of a rotatable drum 16, having a photoconductive surface 17 such as selenium on which latent electrostatic images of a document 18 being copied are produced. Drum 16 is rotated in the direction shown by the solid line arrow by a suitable drive means (not shown).

A scan slit 20 is provided through which document 18 is viewed, suitable document transport means represented by a Constant Velocity Transport (CVT) roll 22 being provided to move document 18 past scan slit 20. An illumination means, exemplified herein by lamp 27, is provided to illuminate the scan slit 20 and the document portion thereover. Image rays reflected from document 18 are transmitted by a suitable optical system, exemplified herein by a gradient index fiber array 24, onto drum 16 at an exposure station 26, the photoconductive surface 17 of drum 16 having been previously uniformly charged at charging station 28 by suitable charging means such as charge corotron 30.

The latent electrostatic image created on the photoconductive surface 17 of drum 16 is thereafter developed by a suitable developing means such as magnetic brush roll 34 at a developing station 32 followed which the developed image is carried on drum 16 to a transfer station 36. There the developed image is transferred to a suitable copy substrate material shown here in the form of a copy sheet 40 brought forward in timed relation thereto along a copy sheet path 51 for this purpose. Charge transfer corotron 42 and detack corotron 43 are provided at transfer station 40 to facilitate transfer of the developed image from drum 16 to copy sheet 40 and to facilitate separation of copy sheet 40 from drum 16.

Following transfer, residual developer materials remaining on the photoconductive surface 17 are removed by cleaning brush 46 at cleaning station 44 preparatory to charging at charge station 28. The developed image transferred to copy sheet 40 is thereafter made permanent as by fusing or fixing at fusing station 60. In the example shown, fusing station 60 has an upper fusing roll 62 with internal heating element 63 and a cooperating lower pressure roll 64. Following fusing, the finished copies are discharged into copy output tray 66.

A copy sheet supply tray 50 is provided with a suitable sheet feeder 52 to feed one sheet 40 at a time from tray 50 into the copy sheet path 51 on demand. Suitable copy sheet transport means, illustrated here by pretransfer roll pair 54, post transfer roll pair 55, and discharge roll pair 57, are provided at discrete points along copy sheet path 51 for transporting the copy sheets 40 along copy sheet path 51 to transfer station 36 and from transfer station 36 to fusing station 60.

While a copying or reproduction machine 10 is shown and described herein, other xerographic based machines such as a printer, recorder, etc. may be contemplated instead. Further, the various operating components described in connection with copying machine 10 are intended as examples only and other xerographic system parts and sub-assemblies may be readily envisioned.

It is recognized that operation of the aforedescribed xerographic system and particularly operation of transfer station 36, detack corotron 43, and/or fusing station 60, is dependent to some degree on certain physical properties of copy sheet 40, particularly copy sheet moisture. As will appear, moisture sensor 12 identifies the moisture content of the copy sheet in process, enabling the current operating parameters of one or more of the xerographic system subsystems and/or components to be adjusted in accordance therewith to assure and maintain optimum system performance.

Figure 2:
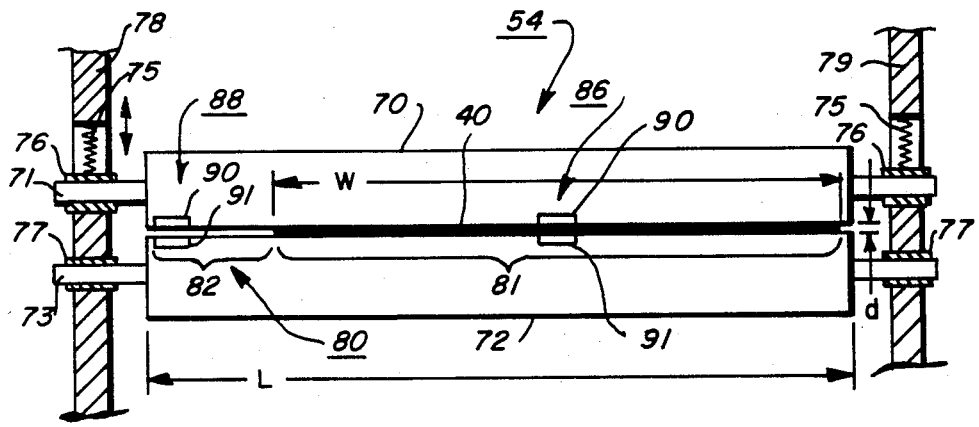
FIG. 2 is a view showing details of the axially extended copy sheet feed roll pair for the copying machine shown in FIG. 1 with capacitors in each of the copy sheet feeding and non-feeding nips of the roll pair.

Referring particularly to FIG. 2 of the drawings, pretransfer roll pair 54 comprises cooperating upper feed roll 70 and lower feed roll 72 respectively, shafts 71, 73 of rolls 70, 72 being rotatably carried by upper and lower journals 76, 77. Upper journal 76 is a floating type support capable of limited up and down movement in machine frame members 78, 79 while lower journal 77 is fixed in frame members 78, 79. Suitable springs 75 bias upper feed roll 70 through shaft 71 into contact with lower feed roll 72, rolls 70, 72 cooperating to form a nip 80 between which the copy sheets 40 pass. The length (L) of upper and lower rolls 70, 72 in the axial direction is greater than the maximum dimension (W) of the largest size copy sheet 40 to be processed by machine 10. As a result, nip 80 includes a nip feeding segment 81 for feeding copy sheets 40 and a nip non-feeding segment 82 at one end thereof. Rolls 70, 72 are formed from a suitable non-conductive material.

A capacitor 86 is provided in the nip feeding segment 81 with a second capacitor 88 in nip non-feeding segment 82, plates 90, 91 of each capacitor 86, 88 being integral with and forming part of the exterior surface of feed rolls 70, 72 respectively. Accordingly, the gap or space (d) between the opposing plates 90, 91 of each capacitor 86, 88 reflects the current gap or nip size between feed rolls 70, 72, it being understood that the nip size (d) varies from zero (0) when no copy sheet is present in the nip feeding segment 81 to a nip size commensurate with the thickness of the copy sheet 40 passing through nip feeding segment 81. Capacitor plates 90, 91 are sized to provide a surface area sufficient to provide a capacitance reading of desired magnitude.

The capacitance signal output of capacitor 88 is a function of the size of the open gap (d) between upper and lower feed rolls 70, 72 while the capacitance signal output of capacitor 86 is a function of both the size of the gap (d) between the rolls 70, 72 and the dielectric current $E_R$ of the copy sheet 40 in the nip feeding segment 81. Since the capacitive signal output of capacitor 88 provides a measure of the gap (d) between rolls 70, 72 at any one time, the dielectric constant $E_R$ of the copy sheet can be determined by comparing the capacitance signal outputs of capacitors 86, 88 with one another.

For example, for parallel plate capacitors of the same geometry, the capacitances $C_1$, $C_2$ of capacitors 88, 86 respectively are determined by the following relationships:

$$C_1 = E_o A \quad (1)$$

$$C_2 = E_R E_o A \quad (2)$$

where
  C = capacitance,
  A = area of the capacitor plates 90, 91,
  K = the dielectric constant of the insulating medium which separates plates 90, 91, and
  d = the space separating the capacitor plates 90, 91.

Combining equations 1 and 2 yields the dielectric current ($E_R$):

$$E_R = C_2/C_1 \quad (3)$$

Assuming that the air gap in nip feeding segment 81 between the copy sheet 40 and rolls 70, 72 to be so small as to have negligible effect on capacitance calculations, the dielectric constant ($E_R$) of copy sheet 40 is represented by the ratio of the capacitance signal output of capacitor 88 to the capacitance signal output of capacitor 86 as shown by Equation 3. And since, for a given type of copy sheet material such as paper, the dielectric constant ($E_R$) is determined primarily by the moisture content of the paper, the moisture content of the copy sheet being fed can be determined.

Figure 3:
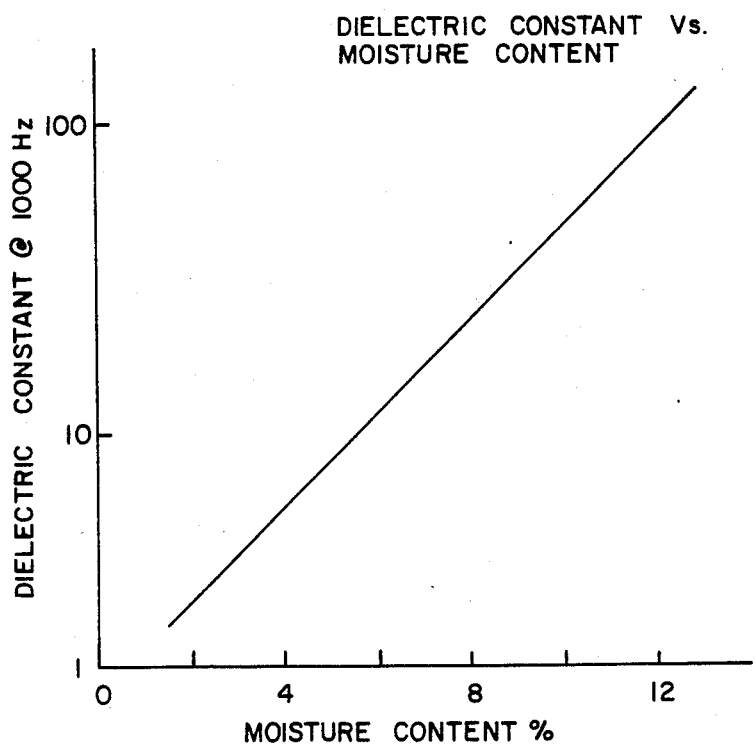
FIG. 3 is a plot depicting the relationship between the dielectric constant and moisture content for a typical copy sheet material.

In FIG. 3, a graph depicts the relationship between the dielectric constant ($E_R$) and the moisture content for a typical cotton fiber based paper having 53% void fraction. Accordingly, with the dielectric constant known, the moisture content of a copy sheet 40, presuming that the copy sheet material is a cotton fiber with 53% void fraction, can be determined from the graph of FIG. 3.

Figure 4:
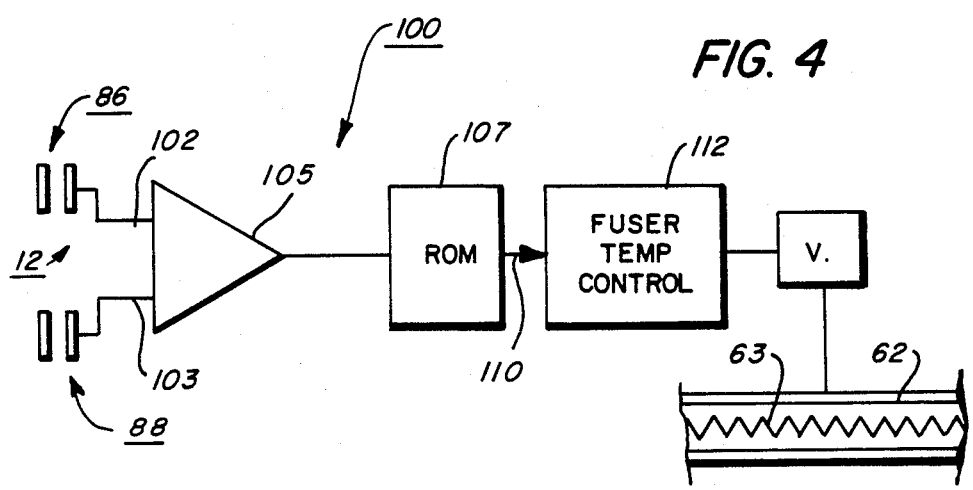
FIG. 4 is a diagram of a control system for generating a control signal representative of the copy sheet moisture content as derived from the signal outputs of the nip capacitors.

Referring to FIG. 4 of the drawings, there is shown a control logic 100 for controlling one or more of the xerographic system components, exemplified here by fuser 60, in response to the moisture content of the copy sheet 40 being processed as detected by moisture sensor 12. Logic 100 includes a suitable comparator 105 for comparing the capacitive signal outputs of capacitors 86, 88 input thereto through leads 102, 103 to provide the dielectric constant ($E_R$). Leads 102, 103 include suitable means (not shown) such as a wiper for electrically connecting the rotating capacitor plates 90, 91 with the stationary components of logic 100. The output of capacitor 105 is employed as an address for addressing a suitable ROM type memory 107 within which control signals representing different dielectric constants are stored. Memory 107 accordingly serves in effect to translate the current dielectric constant output of comparator 105 to a control signal, the level of which represents the dielectric constant for the copy sheet 40 currently passing through the nip feeding segment 81 of pre-transfer roll pair 54. The control signal output of memory 107 in output lead 110 is fed to one or more xerographic system controllers, represented here by temperature control 112 which regulates power input to heating element 63 of fuser roll 62 in accordance with the control signal input thereto.

While pre-transfer roll pair 54 is modified herein to incorporate capacitors 86, 88 of moisture sensor 12 and hence provide control from a point in paper path 51 between sheet feeder 52 and transfer station 36, control may be exercised from different points along the paper path, as for example at post transfer roll pair 55. In that event, the post transfer roll pair would be modified in the same manner as pre-transfer roll pair 54 described above. Alternately, more than one control point may be envisioned. For example, both pre-transfer roll pair 54 and post transfer roll pair 55 may be modified as described herein for this purpose. And while roll type copy sheet feeders are shown and described herein, other types of copy sheet feeders such as belts, webs, etc. alone or in combination with rolls may instead be contemplated.

Figure 5:
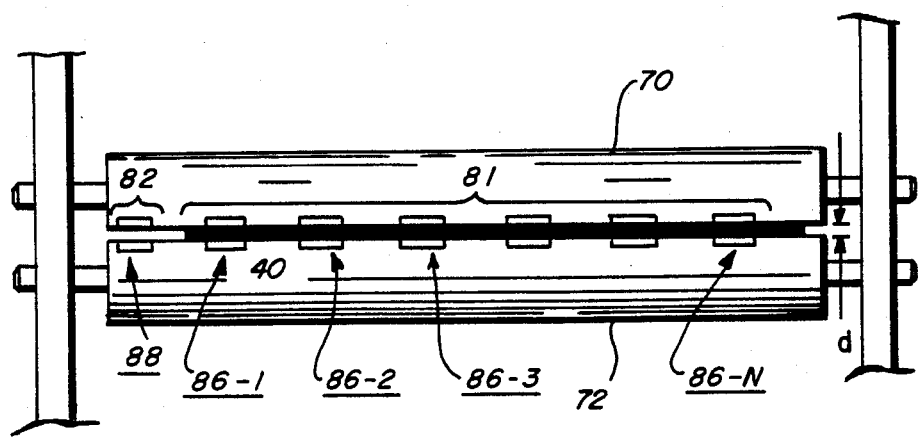
FIG. 5 is an alternate embodiment in which plural nip size detecting capacitors are spaced axially along the copy sheet feed rolls to provide a moisture profile of the copy sheet.

Referring to the embodiment shown in FIG. 5, where like numbers refer to like parts, a succession of capacitors 86-1, 86-2, ... 86-n are disposed at predetermined spaced points along the nip feeding segment 81 to give a profile of the moisture content of the copy sheets. The capacitive signal outputs of capacitors 86-1, 86-2, ... 86-n are compared with the capacitve signal output of capacitor 88 in the nip non-feeding segment 82 to provide the dielectric constant at a series of spaced points across the copy sheet. The dielectric constants are averaged with the average dielectric constant being used to address a memory such as ROM 107 (FIG. 4) to obtain a control signal representative thereof.

While capacitor plates 90, 91 are illustated as being integral with the surface of rolls 70, 72, plates 90, 91 may be located within the roll interior where the thickness of the rolls is relatively thin. In that event, the support for capacitor plates 90 associated with upper feed roll 70 would be arranged to move in concert with roll 70 to assure displacement of capacitor plates 90 as the roll 70 is displaced with the passage of copy sheets therebetween. The capacitor plate 91 associated with lower feed roll 72 would be suitably supported in predetermined fixed position on lower support 77.

Figure 6:
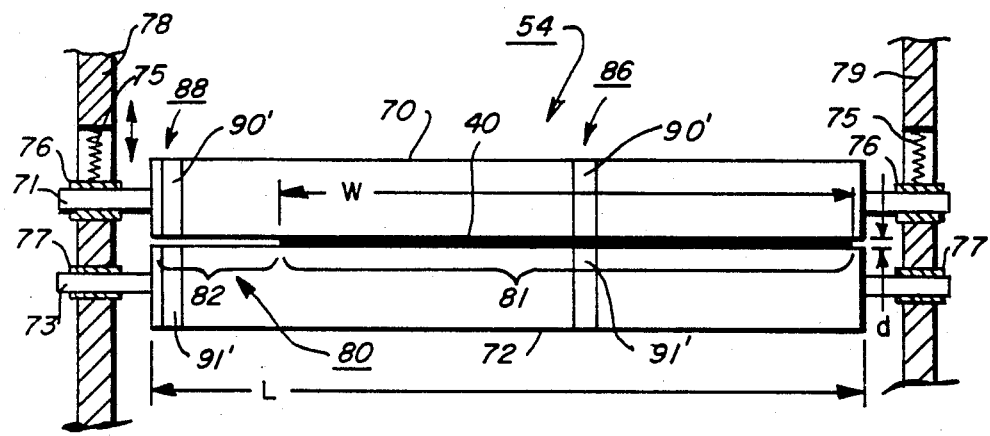
FIG. 6 is a view depicting an alternate embodiment in which the capacitors are in the form of rings extending around the circumference of each roll of the roll pair.

Referring to FIG. 6 of the drawings, where like numerals refer to like parts, capacitor plates 90, 91 may instead be in the form of rings 90', 91' extending around the circumference of the rolls 70, 72. Alternately, the capacitor plates 90, 91 of each capacitor 86, 88 may comprise a series of discrete plate-like members spaced about the circumference of rolls 70, 72.

While the invention has been described with reference to the structure disclosed, it is not confined to the details set forth, but is intended to cover such modifications or changes as may come within the scope of the following claims.

We claim:

1. In an electrostatic copying or printing apparatus including a copy sheet path with at least one pair of rotatable copy sheet transport members, said copy sheet transport members forming a first nip segment between which the copy sheets being fed pass, and a second nip segment through which the copy sheets do not pass, the combination of:
   (a) a first capacitor for generating a signal representative of the nip size of said first nip segment whereby, when a copy sheet is passing through said first nip segment, the signal output of said first capacitor represents the capacitance of said copy sheet;
   (b) a second capacitor for generating a signal representative of the nip size of said second nip segment;
   (c) means for comparing the signal outputs of said first and second capacitors to determine the dielectric constant of said copy sheet as said copy sheet passes through said first nip segment; and
   (d) means for determining the moisture content of said copy sheet from said dielectric constant.

2. The apparatus according to claim 1 in which each of said first and second capacitors have at least one capacitor plate on either side of said first and second nip segments in opposed capactive relation at least during a portion of each revolution of said copy sheet transport members.

3. The apparatus according to claim 2 in which said capacitor plates comprise a plate-like capacitor element within the interior of each of said copy sheet transport members.

4. The apparatus according to claim 2 in which capacitor plates are integral with and form a part of the exterior surface of each of said sheet transport members.

5. The apparatus according to claim 2 in which said capacitor plates comprise a series of plate-like capacitor elements spaced axially along each of said sheet transport members in said first nip segment, each of said plate-like capacitor elements of one sheet transport member being diametrically opposed to a mating plate-like capacitor element of the other of said sheet transport members.

6. The apparatus according to claim 5 in which said plate-like capacitor elements are integral with and form a part of the exterior surface of each of said sheet transport members.

7. The apparatus according to claim 2 in which said capacitor plates each comprise a ring-like capacitor element extending circumferentially around said sheet transport members, said ring-like capacitor elements being integral with and forming a portion of the periphery of said sheet transport members.

8. The apparatus according to claim 2 in which said capacitor plates each comprise a series of plate-like capacitor elements spacedly disposed around the circumference of each of said sheet transport members, said plate-like capacitor elements being integral with and forming a portion of the surface of said sheet transport members.

* * * * *